United States Patent [19]

Jahns et al.

[11] 4,105,800

[45] Aug. 8, 1978

[54] IMMOBILIZED ENZYME METHOD TO ASSESS FISH QUALITY

[75] Inventors: Frederick D. Jahns, Peacedale; Arthur G. Rand, Jr., Kingston, both of R.I.

[73] Assignee: Board of Regents for Education of the State of Rhode Island, Providence, R.I.

[21] Appl. No.: 708,618

[22] Filed: Jul. 26, 1976

[51] Int. Cl.² .................... G01N 33/12; A22C 25/00; C07G 7/02
[52] U.S. Cl. ............................. 426/61; 23/253 TP; 195/63; 195/68; 195/103.5 R; 195/127; 426/231; 426/643
[58] Field of Search .................... 195/63, 99, 103.5 R, 195/127; 23/231, 253 TP, 230 R; 426/61, 231, 643

[56] References Cited

U.S. PATENT DOCUMENTS

| | | | |
|---|---|---|---|
| 2,609,275 | 9/1952 | Golding | 195/103.5 R |
| 2,626,855 | 1/1953 | Hand | 23/253 TP X |
| 3,183,173 | 5/1965 | Oakes | 195/103.5 R |
| 3,413,198 | 11/1968 | Deutsch | 195/63 X |
| 3,964,870 | 6/1976 | Tiedemann et al. | 23/253 TP |

OTHER PUBLICATIONS

Beuchat, L. R., Hypoxanthine Measurement in Assessing Freshness of Chilled Channel Catfish, J. Agr. Food Chem., vol. 21, No. 3, 1973, pp. 453–455.

*Primary Examiner*—David M. Naff
*Attorney, Agent, or Firm*—Thompson, Birch, Gauthier & Samuels

[57] ABSTRACT

This invention relates to a process and article of manufacture useful for quickly and easily assessing the quality of fish intended for human consumption. An enzyme and a dye are first fixed on a carrier. The treated carrier then changes color upon contact with fish in the presence of moisture. The resulting color of the treated carrier has been found to be a sensitive and reliable indicator of fish quality.

5 Claims, 2 Drawing Figures

IMMOBILIZED ENZYME METHOD TO ASSESS FISH QUALITY

BACKGROUND OF THE INVENTION

At the present time, the only available means for readily assessing fish quality is the human sense of smell. Government agencies charged with assuring high standards of quality for fish intended for human consumption employ specially-trained and highly-experienced persons for this purpose. By the time fish reaches the home or supermarket, however, significant additional deterioration of the fish may have taken place. Also, only a relatively small percentage of the total fish for consumption can be governmentally-inspected. For the average individual, the human sense of smell is an imprecise and unreliable indicator of fish quality because by the time the fish develops an odor sufficiently objectionable to the average person, the fish has usually deteriorated well beyond the point of palatability. Thus, there is a need for a means of assessing fish quality which is quick, easily used by the average individual, free of expensive or complex equipment and, most important, highly accurate.

Much work has been done on various chemical methods for determining the quality of fish. For example, U.S. Pat. No. 2,626,855 for a "Seafood Spoilage Indicating System" employs a wooden stick impregnated with a chemical indicator which, by changing color, indicates the presence of acid conditions normally indicating putrefaction. This patent, however, is only capable of determining when "spoilage" has occurred, that is, when the seafood has so far deteriorated that it is no longer safe to consume. It is not-possible by the method of this patent to determine the "freshness" of the seafood short of spoilage conditions. For example, while it may be safe to consume fish which has been dead for several days but is not yet spoiled, "fresh" fish is more palatable and generally more tasty. Similarly, U.S. Pat. No. 2,485,566 for a "Method and Device for Indicating Spoilage" is not suitable for determining the quality of fish apart from spoilage conditions.

Efforts have also been made to determine the "freshness" of fish. One such method has focused on measuring the concentration of hypoxanthine in fish. Hypoxanthine is formed in dead fish by the breakdown of adenosine triphosphate (ATP), a natural biological substance found in live fish. Initially there is a build up in the level of hypoxanthine after the fish is harvested, but as bacteria begin to multiply and consume the hypoxanthine, the level drops off. Therefore, hypoxanthine levels in fish are indicative of freshness in terms of how long the fish has been dead as well as spoilage in terms of the multiplication of bacteria. Attempts to use hypoxanthine levels in assessing fish quality are reported in the following publications: L.R. Beuchat, "Hypoxanthine Measurement in Assessing Freshness of Chilled Channel Catfish," J. Agr. Food Chem., Vol. 21, p. 453 (1973); L.C. Dugal, "Hypoxanthine In Iced Freshwater Fish," J. Food Res. Bd. Can., Vol. 24, p. 2229 (1967); J. Spinelli, M. Eklund and D. Miyauchi, "Measurement of Hypoxanthine In Fish as a Method of Assessing Freshness," J. Food Sci., Vol. 29, p. 710 (1964); and T. Saito, K. Arai and M. Matsuyoshi, "A New Method for Estimating The Freshness of Fish," Bull. Japan Sci. Fish., Vol. 23, p. 265 (1959).

Each of these publications, however, discuss methods requiring sophisticated equipment or controls normally found only in a laboratory. A somewhat less complicated method for determining the levels of compounds in biological fluids is described in U.S. Pat. No. 3,099,605. Filter paper strips are impregnated with a solution comprising two enzymes, an indicator whose color is affected by hydrogen peroxide in the presence of one of the enzymes, a buffer and a stabilizer. For example, in testing for hypoxanthine, the patent suggests using a solution of xanthine oxidase, orthotolidine dihydrochloride, peroxidase and a buffer. The solution is said to turn blue in the presence of xanthine or hypoxanthine. The principal difficulty with this method is that it requires the simultaneous use of two enzymes, one to form hydrogen peroxide and the second to activate the dye system for making measurements. A two-enzyme system of this type is more difficult to prepare and control and is not as stable in storage as a single enzyme system.

OBJECTS OF THE INVENTION

Accordingly, it is a principal object of this invention to provide a single enzyme system for determining hypoxanthine levels.

It is another object of this invention to provide a simple, economic, and accurate method for assessing fish quality which is based on using a single enzyme system for determining hypoxanthine levels.

A further object of this invention is to provide treated carriers impregnated with a single enzyme system for determining hypoxanthine levels, which treated carriers are especially adaptable to assessing fish quality.

Other objects of this invention will become apparent from the following description.

SUMMARY OF THE INVENTION

This invention is based on the discovery that a single enzyme system for determining hypoxanthine levels can be prepared using resazurin dye. While resazurin has been used for determining the quality of dairy products, for example in U.S. Pat. No. 2,609,275, because of its special property of changing color as the oxygen is used up in its surrounding environment, it has never been used in connection with determining hypoxanthine levels. In this invention, an aqueous solution comprising resazurin, an enzyme, a buffer and optionally including gelatin and/or a stabilizer, is used to impregnate a suitable carrier. The carrier is then freeze dried and stored for later use. To determine the hypoxanthine level in a biological environment, the carrier is brought into contact with the environment, for example either fish meat itself or a protein-free extract of the fish, in the presence of moisture. The carrier will change color depending on the level of hypoxanthine present. By comparing the color of the carrier to a standardized chart, the hypoxanthine level can be readily determined.

In an alternative embodiment especially useful in assessing the quality of fish, an elongated support holds two carriers, one impregnated with resazurin and an enzyme sensitive to hypoxanthine while the second is impregnated with a dye and an enzyme sensitive to the diamine compounds which are typically formed in the presence of bacteria. Each carrier on the support is, in turn, brought into contact with the fish being tested. The hypoxanthine-sensitive carrier will change color indicating the level of hypoxanthine, and the second carrier will change color indicating the level of diamines. Taken together, these two indicators give a highly accurate assessment of fish quality without referring to a standardized chart.

DESCRIPTION OF THE PREFERRED EMBODIMENT

Figure 1:
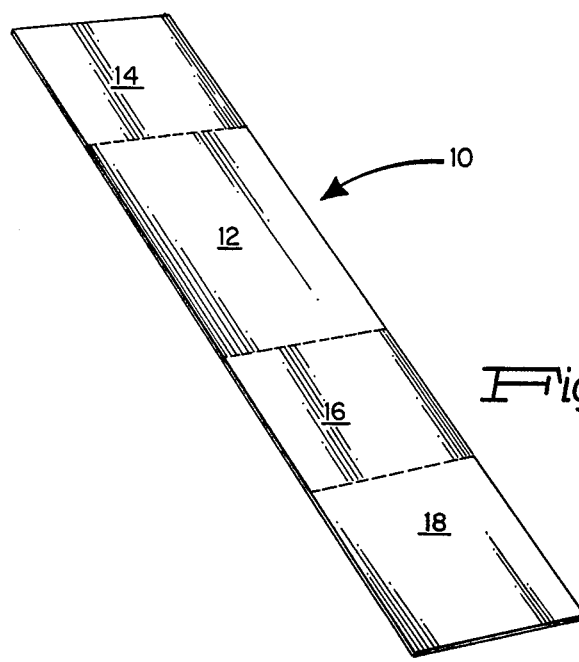
FIG. 1 is a schematic view of a support for assessing fish quality prepared according to this invention.

While this invention may be used to test for hypoxanthine levels alone by using a single enzyme-resazurin system and a standardized reference chart, in the preferred embodiment of this invention, fish quality is assessed by treating two different carriers to test respectively for both hypoxanthine and diamine levels. FIG. 1 illustrates a support holding two carriers prepared in accordance with this preferred practice.

The support 10 is an elongated stick, splinter or strip of plastic, wood or similar material. Typically the carriers 14 and 16 will be an absorbent type of paper. In general, any absorbent material which has the characteristics of being substantially colorless and predominantly inert with respect to the other reagents and biological substances employed in this invention is suitable as the carrier.

One carrier 14 is impregnated with an enzyme sensitive to hypoxanthine and resazurin. The impregnation may be achieved in any conventional manner, for example by dipping the carrier into an aqueous solution of enzyme and resazurin for a sufficient period of time, such as about 10 seconds, until the submerged end is substantially saturated with solution. Alternatively, the aqueous solution may be sprayed onto a readily-absorbent carrier such as strips of filter paper. The treated carrier is then freeze dried as described below.

Typically the enzyme which is specific for hypoxanthine will be xanthine oxidase, Classification No. [EC 1.2.3.2]. Any enzyme sensitive to hypoxanthine, however, may be used. To stabilize the enzyme both in solution and on the carrier, it is preferred to employ an aqueous buffer solution and, optionally, a stabilizer for the enzyme. For example, xanthine oxidase can be stabilized by applying it in about a 0.15 M phosphate solution having a pH of about 7.6 and by the addition of a stabilizer such as ammonium sulfate, sodium salicylate or ethylenediaminetetraacetate (EDTA). It has also been found advantageous to add gelatin, for example about 0.01–1 g. per 1 ml. of solution, to the aqueous solution. The absorbed gelatin helps to retain the enzyme and resazurin dye in the carrier and minimizes leaching while tests are being conducted.

The specific proportions of enzyme and resazurin in the aqueous solution are not critical and may be varied by routine experimentation to optimize the results under particular conditions. In general, however, about 50–500 $\mu$g of resazurin per 1 ml. of solution may be employed, preferably about 11–17 mg. resazurin per 100 ml. of solution. Also, in general, about 0.1–7 international units of enzyme per 1 ml. of solution are typically employed in this invention. The pH of the buffer solution should be adjusted depending on the specific enzyme which is selected. Any buffer suitable to the particular pH range and inert to the other reagents may be used. The amount of stabilizer added, if any, should be sufficient to stabilize the enzyme. Similarly, the amount of gelatin added, if any, should be sufficient to minimize leaching of enzyme and resazurin from the carrier.

The carrier 14 is then freeze dried or lyophilized. Because enzymes are usually sensitive to heat, the drying should be accomplished by some form of "freeze-drying." For example, a conventional freeze dryer may be employed. It is preferred, however, to initially freeze the treated carrier by contacting it with liquid nitrogen prior to the vacuum dehydration. This method of drying has been found to result in superior enzyme stabilization. Finally, carrier 14 is adhesively secured to support 10.

The other carrier 16 of support 10 in FIG. 1 is impregnated with an enzyme sensitive to the diamine compounds and a suitable dye. The impregnation may be carried out as described above for carrier 14. Similarly, it is preferred to employ an aqueous buffer solution optionally containing a stabilizer for the enzyme and gelatin, also as described above. In securing carriers 14 and 16 to support 10 it is preferred to leave an untreated middle portion 12 for purposes of separating the reaction zones and also to have an end portion 18 for purposes of handling the carrier strips and support.

The preferred enzyme for impregnating carrier 16 is diamine oxidase, Classification No. [EC 1.4.3.6], and the preferred dye is resazurin. This again has the advantage of being a single-enzyme system. It is within the scope of this invention, however, to employ other combinations of dyes and enzymes for treating carrier 16. The lyophilization step is also carried out in a freeze dryer with the initial freezing step conducted preferably in liquid nitrogen. The supports 10 holding treated carrier strips 14 and 16 are then packaged in a dessicated bottle and stored for use.

In order to test the quality of a portion of fish in accordance with this invention, the fish may be tested either directly or else a protein-free extract can be prepared by conventional techniques using perchloric acid.

Carrier 14 of support 10 is either dipped into the protein-free fish extract or else carrier 14 is placed into a slit in the fish tissue and moistened. It will be apparent that the concentration of hypoxanthine, therefore the color response of carrier 14, will vary depending on which method is being used. Where it is desirable to correlate hypoxanthine level with freshness in terms of the number of hours which have elapsed since the fish was harvested, it is necessary to prepare a standardized testing procedure and a standardized color chart for comparison. Where a qualitative determination of freshness is not required, however, the general color of carrier 14 gives a good indication of quality, especially if both carriers 14 and 16 are tested and compared as discussed below.

Figure 2:
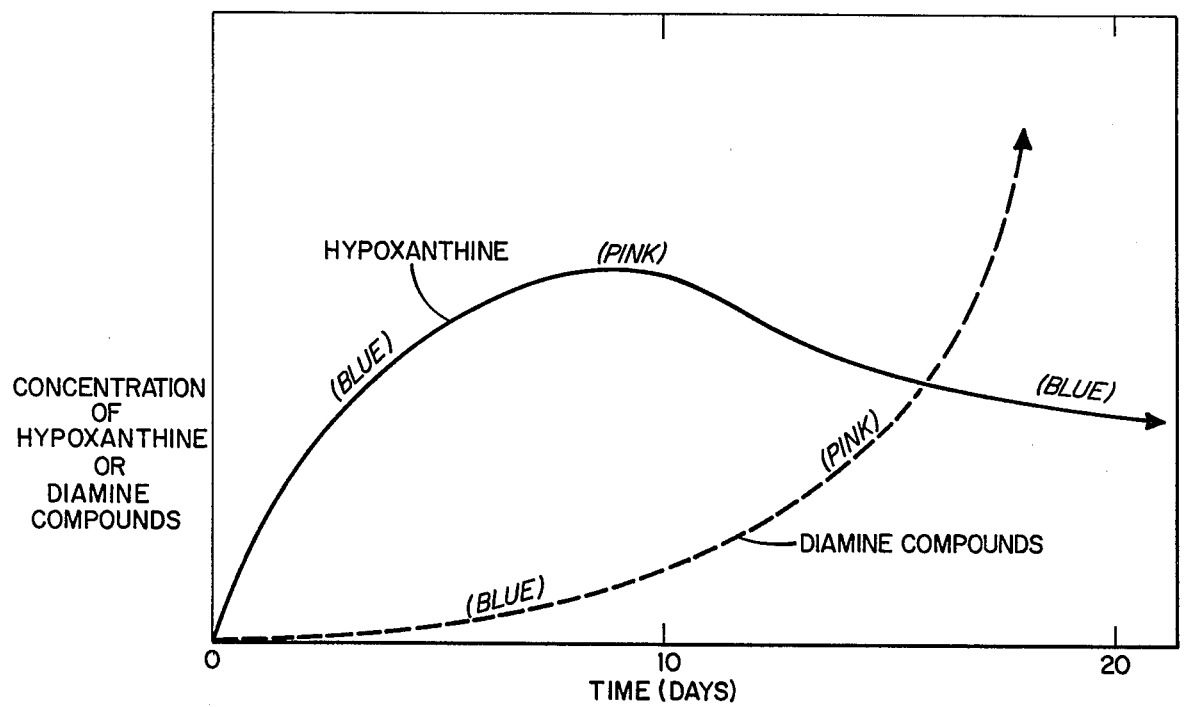
FIG. 2 is a generalized graph which illustrates the typical variation of hypoxanthine levels and diamine levels in post-harvest fish over time.

Referring now to FIG. 2, this graph illustrates the typical variation in the levels of hypoxanthine (solid curve) and diamine compounds (broken curve) in post-harvested fish stored in ice. It will be understood that the levels of hypoxanthine and diamine compounds in particular instances will vary somewhat depending on such factors as the type of fish, the temperature, humidity and other environmental conditions, and the manner in which the tests are performed. In general, however, the hypoxanthine level initially increases rapidly, gradually tapers off and reaches a maximum, then drops off to a more or less constant intermediate level. The level of diamines, by contrast, at first increases slowly but then increases more rapidly soon reaching an asymptotic slope. This is the exponential behavior typically associated with geometric bacterial growth.

It has been found that resazurin turns blue when exposed to an environment containing relatively low levels of hypoxanthine or of diamines and pink at higher levels of these substances. The color change is not an abrupt one. Rather, the blue color gradually brightens into blue-pink at intermediate levels of hypoxanthine or diamines.

This color change is reflected in FIG. 2 by labeling alongside each curve. Referring to the hypoxanthine (solid) curve, it will be seen that during about the first several days of cold storage after harvesting of the fish the hypoxanthine level increases rapidly. During this time, carrier 14 of support 10 in FIG. 1 will produce a blue hue when brought into contact with the fish sample. If desired, the color of the carrier may be compared to a standardized chart to more accurately determine freshness. During roughly the next four days, the blue hue slowly brightens into a bright pink indicating the maximum level of hypoxanthine. Thereafter, the color gradually fades back into blue indicating a decrease in hypoxanthine levels as bacteria begin to appear in substantial quantities.

Referring now to the diamine (broken) curve, it will be seen that during about the first several days of cold storage after harvesting of the fish, bacteria levels, consequently diamine levels, remain relatively low. During this time, carrier 16 of support 10 in FIG. 1 will produce a blue hue when brought into contact with the fish sample. As cold storage time increases, the bacteria and diamine levels of fish begin to increase, and the blue hue becomes pink and remains pink as diamine levels continue to increase.

Thus, because of these clear, accurate and reproducible color changes, the quality of a fish sample is readily determined. When carriers 14 and 16 of support 10 in FIG. 1 both turn blue, the fish is very fresh and not spoiled. When carrier 14 turns pink but carrier 16 turns blue, the fish is in an intermediate condition where it is not fresh but has not yet spoiled and probably may be consumed. When carrier 14 turns blue and carrier 16 turns pink, however, the fish is definitely well on its way to becoming spoiled and should probably not be consumed. Thus, by this simple technique, an assessment of fish quality can be readily and accurately made.

EXAMPLE 1

Test strips in accordance with this invention were prepared as follows: Resazurin was dissolved in 100 ml of hot 0.17 M phosphate buffer (pH 7.6) at a concentration of 11.6 mg for one group of samples (Group A) and 17.2 mg for a second group of samples (Group B). The solution was cooled to room temperature and 7.598 g of ammonium sulfate was added. Gelatin (50 mg/ml) was dissolved in boiling water, cooled to room temperature and 0.5 ml was added to 4.0 ml of the resazurin solution, followed by 0.5 ml of xanthine oxidase solution (10 U/ml). Chromatographic paper strips, dried at 100° C. overnight, were soaked for 10 seconds in the above solution, immediately frozen at −40° C., and dried in a freeze dryer for 12 hr. The strips were then stored in jars containing silica gel desiccant at approximately −20° C. until used for analysis.

EXAMPLE 2

Fish samples were prepared for testing in the following manner: Two separate catches of winter flounder (pseudopleuronectes americanus) were employed for analysis. The first catch, for Group A tests, was caught by hook and line. Fish were landed as quickly as possible and packed in crushed ice (approx. 0° C.) without being stunned. The second catch, for Group B tests, were trawl-caught. The fish were stunned approximately one hour after landing and packed in crushed ice.

Group A fish remained in ice storage for the incubation period and one fish was removed from the ice approximately every other day and placed in a freezer at −20° C. for preservation and storage until analyzed. The fish were allowed to thaw at room temperature for 2.5 hrs., after which samples were prepared for analysis. Group B fish also remained in iced storage for the incubation period, with one fish removed at approximately 48 hr. intervals for immediate analysis.

One separate fish for each test period was filleted and a 20-g sample from the dorsal portion of the fish was blended with 80 ml of cold 0.6 N perchloric acid. The homogenate was filtered through a What #2 filter. The extracts prepared were used for both a conventional quantitative colorimetric determination of hypoxanthine concentration and the visual enzyme strip method of hypoxanthine measurement of this invention.

EXAMPLE 3

Fish samples were tested according to one of the conventional colorimetric techniques for analyzing hypoxanthine levels as follows: A 25-ml aliquot of each filtered fish extract was taken, and $KClO_3$ was precipitated with adjustment of the pH to 7.6 with 20% KOH on a pH meter. The samples were then buffered with addition of 3 ml of 0.17 M potassium phosphate buffer, pH 7.6. This buffered substrate was made up to 50 ml with water and 0.1 ml of this solution was assumed to contain 10 mg of fish.

The general analytical procedure was as follows: The substrate (0.1 ml) and 1.0 ml of DIP (23 µg/ml of 0.17 M phosphate buffer, pH 7.0) were added to a cuvette, followed by distilled water to bring the volume up to 2.0 ml. The test was started with addition of 0.5 ml of xanthine oxidase (0.27 units/ml of 0.17 M phosphate buffer, pH 7.6), and allowed to run at room temperature for 3 minutes while being constantly monitored at 604 nm on a Cary 15 recording spectrophotometer against a blank containing everything except DIP and substrate. The initial velocity of each reaction was computed as the absorbance change per minute. The initial velocity for a standard hypoxanthine solution (25 µg/ml distilled water) was also run and employed to compute the concentration in the fish samples by the usual technique.

The colorimetric analysis of hypoxanthine concentration found in the two storage trials of iced winter flounder showed that a steady increase in hypoxanthine concentration occurred with storage time until the values leveled off at 4.7 to 5.0µM/g (70 mg%) from 198 to 251 h, the area where organoleptic spoilage became obvious. The hypoxanthine concentration in winter flounder then dropped to a value of about 3µM/g (40 mg%) after 300 hours of storage. The general variation in hypoxanthine level conformed fairly closely to that shown by the solid curve in FIG. 2.

EXAMPLE 4

Fish samples were next tested according to the method of this invention. Dry enzyme test strips of Groups A and B as described above were dipped in standard hypoxanthine solutions and filtered fish extracts for 2 seconds to allow uptake of the fluid. The strips were allowed to react at room temperature for 5 minutes. No noticeable change in color of the strips occurred after this point in time. The strip moistened with the fish extract was then compared with color changes obtained with strips dipped in known amounts of hypoxanthine. The hypoxanthine concentration in the original fish sample was estimated and expressed in terms of μg/ml.

When a strip was reacted with a standard hypoxanthine solution of 2.25 g/ml a slight change was observed from the control in 5 minutes. Increasing concentrations of hypoxanthine up to 37.5 g/ml produced progressive color changes from blue to a bright pink when the dye has been completely utilized in the reaction between xanthine oxidase and hypoxanthine. The dye concentration in the formulation of the strip may be manipulated to accommodate the projected hypoxanthine concentration. The degree of change in color of the strips from blue to a pinkish shade closely parallels the change in concentration of hypoxanthine as presented in FIG. 2 and as confirmed by standard colorimetric analysis as described above. This data is tabulated in Table 1 below. Therefore, these tests establish a good correlation between standard colorimetric analysis and the simple and convenient method of this invention.

Table 1

Comparison of hypoxanthine concentration suggested by the visual enzyme test strip with that of the colorimetric analysis:

| Age of Fish | Hypoxanthine Concentration | |
|---|---|---|
| | Visual | Colorimetric |
| 26 h | 25–37 μg/ml | 35.0 μg/ml |
| 48 h | 18.75–25 μg/ml | 23.5 μg/ml |
| 100 h | > 37 μg/ml | 52.0 μg/ml |
| 148 h | > 37 μg/ml | 61.0 μg/ml |
| 198 h | > 37 μg/ml | 64.0 μg/ml |
| 251 h | > 37 μg/ml | 67.0 μg/ml |
| 304 h | 25–37 μg/ml | 37.9 μg/ml |
| 352 h | 25–37 μg/ml | 37.0 μg/ml |

By employing hypoxanthine concentration in fish tissue as an index of freshness in the manner of this invention, much of the cost or lack of objectivity in establishing fish quality can be eliminated. Such a simple test permits more widespread control of fish quality so that determination of the degree of freshness in a particular sample of fish can be accomplished in the processing plant, dockside or even on board ship. A "Freshness Index," might be introduced to express hypoxanthine on a percentage basis, which might be more understandable than the use of μM/g measures of concentration.

Thus a simple visual color change from blue to pink can indicate to the layman that the fish he is testing can no longer be considered fresh.

While this invention has been described with particularity for the testing of fish, this invention is equally applicable to testing shell fish or meats. Even more broadly, this invention is applicable to any analysis which depends on determining hypoxanthine levels or on monitoring changes in hypoxanthine levels.

Having described the invention, what is claimed is:

1. An article of manufacture of assessing the quality of fish comprising an elongated support supporting two carriers, one carrier being impregnated with a freeze dried mixture consisting essentially of resazurin, xanthine oxidase, a stabilizer for xanthine oxidase, and a buffer and the other carrier being impregnated with a freeze dried mixture consisting essentially of resazurin, diamine oxidase, a stabilizer for diamine oxidase and a buffer.

2. The article of claim 1 wherein each of said mixtures includes gelatin.

3. A method for assessing the quality of fish comprising the steps of:
   (a) impregnating a first carrier with an aqueous buffer solution consisting essentially of resazurin, xanthine oxidase and a stabilizer for xanthine oxidase and a second carrier with an aqueous buffer solution consisting essentially of resazurin, diamine oxidase, and a stabilizer for diamine oxidase and thereafter freeze drying both carriers;
   (b) contacting each of the two impregnated carriers with a sample of the fish to be tested in the presence of moisture for a sufficient time until no further color change in each carrier is evident; and,
   (c) comparing the colors of the two carriers to determine the quality of the fish.

4. The method of claim 3 wherein said buffer solutions additionally contain gelatin.

5. The method of claim 3 wherein said freezing is carried out in liquid nitrogen.

* * * * *